United States Patent
Deshpande et al.

(10) Patent No.: US 9,434,728 B1
(45) Date of Patent: Sep. 6, 2016

(54) NITROGEN CONTAINING COMPOUNDS AND THEIR USE

(71) Applicant: WOCKHARDT LIMITED, Aurangabad (IN)

(72) Inventors: Prasad Keshav Deshpande, Aurangabad (IN); Shivaji Sampatrao Pawar, Aurangabad (IN); Satish Bhawsar, Aurangabad (IN); Ravindra Dattatraya Yeole, Aurangabad (IN); Sachin Bhagwat, Aurangabad (IN); Mahesh Vithalbhai Patel, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

(21) Appl. No.: 15/027,790

(22) PCT Filed: Oct. 10, 2014

(86) PCT No.: PCT/IB2014/065195
§ 371 (c)(1),
(2) Date: Apr. 7, 2016

(87) PCT Pub. No.: WO2015/052682
PCT Pub. Date: Apr. 16, 2015

(30) Foreign Application Priority Data

Oct. 11, 2013 (IN) .......................... 3216/MUM/2013

(51) Int. Cl.
| | | |
|---|---|---|
| *C07D 471/08* | (2006.01) |
| *A61K 31/546* | (2006.01) |
| *A61K 31/407* | (2006.01) |
| *A61K 31/439* | (2006.01) |
| *A61K 45/06* | (2006.01) |

(52) U.S. Cl.
CPC ........... *C07D 471/08* (2013.01); *A61K 31/407* (2013.01); *A61K 31/439* (2013.01); *A61K 31/546* (2013.01); *A61K 45/06* (2013.01)

(58) Field of Classification Search
CPC .. C07D 471/08; A61K 45/06; A61K 31/407; A61K 31/546; A61K 31/439
See application file for complete search history.

(56) References Cited

U.S. PATENT DOCUMENTS 8,754,102 B2 * 6/2014 Patil ..................... C07D 471/08
514/203

FOREIGN PATENT DOCUMENTS

| EP | 2135959 | 12/2009 |
| WO | WO/2013/038330 | 3/2013 |

* cited by examiner

*Primary Examiner* — Sudhakar Katakam
(74) *Attorney, Agent, or Firm* — Bio Intellectual Property Services LLC (Bio IPS); O. (Sam) Zaghmout

(57) ABSTRACT

Compound of Formula (I), its preparation and use in preventing or treating bacterial infection is disclosed. Formula (I)

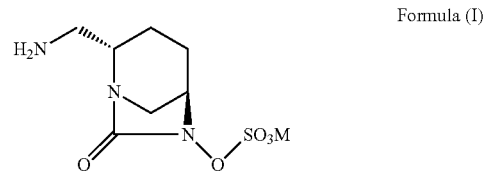

Formula (I)

18 Claims, No Drawings

NITROGEN CONTAINING COMPOUNDS AND THEIR USE

RELATED PATENT APPLICATIONS

This application claims benefit of Indian Patent Application No. 3216/MUM/2013 filed on Oct. 11, 2013, the disclosures of which are incorporated herein by reference in its entirety as if fully rewritten herein.

FIELD OF THE INVENTION

The invention relates to nitrogen containing compounds, their preparation and their use in preventing or treating infections.

BACKGROUND OF THE INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistance. Coates et al. (*Br. J. Pharmacol.* 2007; 152(8), 1147-1154.) have reviewed novel approaches to developing new antibiotics. However, the development of new antibacterial agents is a challenging task. For example, Gwynn et al. (*Annals of the New York Academy of Sciences,* 2010, 1213: 5-19) have reviewed the challenges in discovery of antibacterial agents.

Another approach to overcome the bacterial resistance to known antibacterial agents is to target the bacterial mechanisms, which helps it acquire and maintain the resistance. For example, several bacteria are known to produce enzymes (beta-lactamase enzymes) that hydrolyze the beta-lactam ring in a typical beta-lactam antibacterial agent. Once the beta-lactam ring is hydrolyzed, the antibacterial agents become ineffective against those bacteria. Several compounds, generally known as beta-lactamase inhibitors, are capable of inhibiting activity of one or more beta-lactamase enzymes, thereby restoring the efficacy of conventional beta-lactam antibacterial agents. Typical examples of beta-lactamase inhibitors include Sulbactam, Tazobactam and Clavulanic acid. Drawz et al. (*Clinical Microbiology Reviews,* Jan. 2010, Volume 23(1), p. 160-201) have reviewed the subject of beta-lactamase inhibition. U.S. Pat. No. 7,112,592 and US Patent Application No. 20100092443 disclose several compounds containing heterocyclic core and their use as antibacterial agents. The inventors have now surprisingly discovered nitrogen containing compounds having antibacterial activity.

SUMMARY OF THE INVENTION

Accordingly, there are provided nitrogen containing compounds, methods for preparation of these compounds, pharmaceutical compositions comprising these compounds, and method for preventing or treating bacterial infection in a subject using these compounds.

In one general aspect, there are provided compounds of Formula (I)

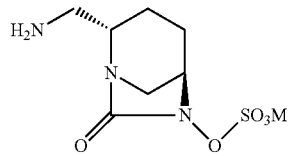

Formula (I)

or a stereoisomer or a pharmaceutically acceptable derivative thereof; wherein M is a cation.

In another general aspect, there are provided pharmaceutical compositions comprising a compound of Formula (I) or a stereoisomer or a pharmaceutically acceptable derivative thereof.

In another general aspect, there is provided a method for preventing or treating bacterial infection in a subject, said method comprising administering to said subject a pharmaceutically effective amount of a compound of Formula (I) or a stereoisomer or a pharmaceutically acceptable derivative thereof. In another general aspect, there is provided a method for preventing or treating a bacterial infection in a subject, said infection being caused by bacteria producing one or more beta-lactamase enzymes, said method comprising administering to said subject a pharmaceutically effective amount of a compound of Formula (I) or a stereoisomer or a pharmaceutically acceptable derivative thereof.

In another general aspect, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof. In another general aspect, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof. In another general aspect, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I) or a stereoisomer or a pharmaceutically acceptable derivative thereof, and (b) at least one beta-lactamase inhibitor or a pharmaceutically acceptable derivative thereof.

In another general aspect, there is provided a method for preventing or treating bacterial infection in a subject, said method comprising administering to said subject a pharmaceutically effective amount of: (a) a compound of Formula (I) or a stereoisomer or a pharmaceutically acceptable derivative thereof and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I) or a stereoisomer or a pharmaceutically acceptable derivative thereof, (b) at least one beta-lactamase inhibitor or a pharmaceutically acceptable derivative thereof, and (c) at least one antibacterial agent or a pharmaceutically acceptable derivative thereof.

In another general aspect, there are provided methods for increasing antibacterial effectiveness of an antibacterial agent in a subject, said method comprising co-administering said antibacterial agent or a pharmaceutically acceptable derivative thereof, with a pharmaceutically effective amount of a compound of Formula (I) or a stereoisomer or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification including the claims, the singular forms "a", "an", and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, within the scope of the invention. In general, a reference to a compound is intended to cover its stereoisomers and mixture of various stereoisomers.

The term "pharmaceutically acceptable derivative" as used herein refers to and includes any pharmaceutically acceptable salt, pro-drug, metabolite, ester, ether, hydrate, polymorph, solvate, complex and adduct of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salts, pro-drugs, metabolites, esters, ethers, hydrates, polymorphs, solvates, complexes and adducts) which, upon administration to a subject, are capable of providing (directly or indirectly) the antibacterial agent.

The term "pharmaceutically acceptable salt" as used herein refers to one or more salts of a given compound which possesses the desired pharmacological activity of the free compound and which are neither biologically nor otherwise undesirable. In general, the term "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutically acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional group capable of being converted into salt, each such functional group may be converted to corresponding salt independently. For example, in case of compounds containing two basic nitrogen atoms, one of the basic nitrogen can form salt with one acid while the other basic nitrogen can form salt with another acid. Some compounds according to the invention contain both acidic as well as basic moieties, and thus can form inner salts or corresponding zwitterions. In general, all pharmaceutically acceptable salt forms of compound of Formula (I) according to invention including acid addition salts, base addition salts, zwitterions or the like are contemplated to be within the scope of the present invention and are generically referred to as pharmaceutically acceptable salts.

The term "OBn" as used herein refers to benzyloxy.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of normal floras, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop or mouthwash. In case of a pharmaceutical composition comprising more than one ingredients (active or inert), one of the way of administering such composition is by admixing the ingredients (e.g. in the form of a suitable unit dosage form such as tablet, capsule, solution, powder or like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term "growth" also includes maintenance of on-going metabolic processes of a microorganism, including the processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject. The term "synergistic" or "synergy" as used herein refers to the interaction of two or more agents so that their combined effect is greater than their individual effects.

The term "antibacterial agent" as used herein refers to any substance, compound or a combination of substances or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure. The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely. The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, for example, to increase the solubility of the compound. Typical, non-limiting examples of solid carriers include, starch, lactose, dicalcium phosphate, sucrose, and kaolin. Typical, non-limiting examples of liquid carriers include sterile water, saline, buffers, non-ionic surfactants, and edible oils such as peanut oil and sesame oils. In addition, various adjuvants commonly used in the art may also be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8$^{th}$ Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

In one general aspect, there are provided compounds of Formula (I)

Formula (I)

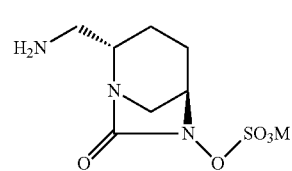

or a stereoisomer or a pharmaceutically acceptable derivative thereof; wherein M is a cation.

In general, the term "cation" includes H, Na, K, Mg, Ca, $NH_4^+$, $(CH_3CH_2)_3N^+$ and the like. In another general aspect, there is provided a compound of Formula (I), wherein M is H, Na, K, Mg, Ca, $NH_4^+$, or $(CH_3CH_2)_3N^+$.

In one general aspect, there is provided a compound of Formula (XI), chemically known as (2S, 5R)-6-sulfooxy-2-(aminomethyl)-7-oxo-1,6-diaza-bicyclo [3.2.1]octane or a stereoisomer or a pharmaceutically acceptable derivative thereof.

In general, the compounds of the invention can be prepared according to the general procedure given in Scheme 1. A person of skills in the art would appreciate that the described method can be varied or optimized further to provide the desired and related compounds.

In some embodiments, the compound of Formula (I), wherein M is hydrogen, was prepared using a general procedure described in Scheme 1. In some embodiments, there is provided a process for the preparation of (2S, 5R)-6-sulfooxy-2-(aminomethyl)-7-oxo-1,6-diaza-bicyclo [3.2.1]octane of Formula (XI) or a stereoisomer or a pharmaceutically acceptable derivative thereof, (Formula XI)

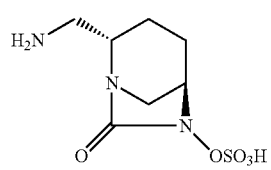

comprising:

(a) Converting a compound of Formula (II) to a compound of Formula (III);

(Formula II)

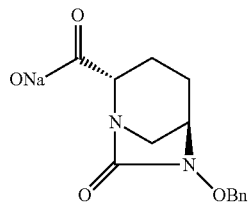

(Formula III)

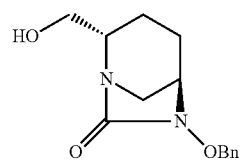

(b) Reacting a compound of Formula (III) with p-nitrophenylsulfonyl chloride in presence of a base to obtain a compound of Formula (IV);

(Formula IV)

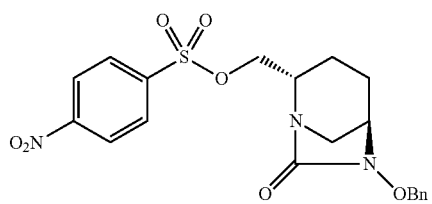

(c) Reacting a compound of Formula (IV) with sodium azide to obtain a compound of Formula (V);

(Formula V)

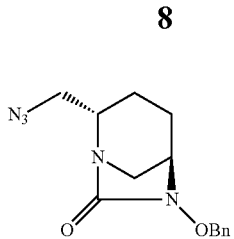

(d) Converting a compound of Formula (V) to a compound of Formula (VI);

(Formula VI)

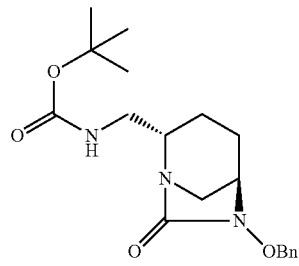

(e) Hydrogenolysis of a compound of Formula (VI) to obtain a compound of Formula (VII);

(Formula VII)

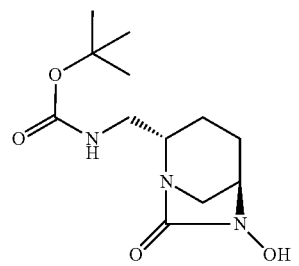

(f) Reacting a compound of Formula (VII) with sulfonating agent, followed by a reaction with tetrabutylammonium hydrogen sulfate to obtain a compound of Formula (VIII);

(Formula VIII)

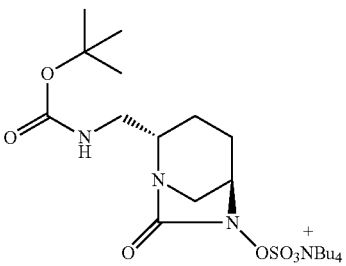

(g) Converting a compound of Formula (VIII) to a compound of Formula (IX);

(Formula IX)

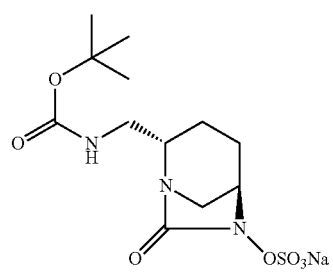

(h) Reacting compound of Formula (IX) with trifluoroacetic acid in suitable solvent to obtain a compound of Formula (X); and

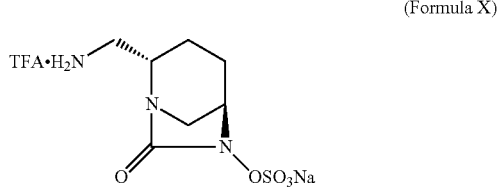

(Formula X)

(i) Converting a compound of Formula (X) to a compound of Formula (XI).

Typically, sodium salt of (2S, 5R) trans-6-benzyloxy-7-oxo-1, 6-diaza-bicyclo[3.2.1] octane-2-carboxylic acid (II) was first treated with a suitable base such as N-methyl morpholine and a suitable formylating agent such as ethyl chloroformate (ClCOOEt) to produce the corresponding mixed anhydride which was subsequently reduced using sodium borohydride to provide an alcoholic compound (III), (2S, 5R)-2-(hydroxymethyl)-6-(benzyloxy)-7-oxo-1, 6-diaza-bicyclo[3.2.1]octane.

The hydroxyl group of the compound of Formula (III) was condensed with p-nitrophenyl sulfonyl chloride (p-NO$_2$PhSO$_2$Cl) in presence of a suitable base such as triethylamine and a suitable solvent such as dichloromethane to provide (2S, 5R)-2-(4-nitrophenylsulfonate methyl)-6-(benzyloxy)-7-oxo-1, 6-diaza-bicyclo [3.2.1] octane (IV). The sulfonate compound of Formula (IV) was reacted with sodium azide (NaN$_3$), wherein the sulfonate group was displaced with the azide group to provide the compound (2S, 5R)-2-(azidomethyl)-6-(benzyloxy)-7-oxo-1,6-diaza-bicyclo[3.2.1] octane (V).

The compound (V) was reacted with triphenylphosphine (PPh$_3$) in a suitable solvent such as tetrahydrofuran followed by addition of a catalytic amount of water to provide corresponding amine. This amino compound was further treated in situ with di-tert-butyl dicarbonate ((Boc)$_2$O) in presence of a suitable base such as triethylamine to provide an amino protected compound, (2S, 5R)-2-(tert-butoxycarbonylaminomethyl)-6-benzyloxy-7-oxo-1, 6-diaza-bicyclo [3.2.1] octane (VI). The intermediate compound of Formula (VI) was subjected to hydrogenolysis using a catalyst such as 5% or 10% Palladium on carbon in presence of a hydrogen source such as hydrogen gas and in a suitable solvent such as methanol to provide debenzylated compound, (2S, 5R)-2-(tert-butoxycarbonylaminomethy)-6-hydroxy-7-oxo-1,6-diaza-bicyclo[3.2.1] octane (VII).

The hydroxyl function in the compound of Formula (VII) was further reacted with a suitable sulfonating agent such as sulfur trioxide-pyridine complex (SO$_3$Py complex) or sulfur trioxide-dimethylformamide complex; in a suitable solvent such as dichloromethane and in presence of a suitable base such as triethylamine (Et$_3$N) to provide the corresponding sulfate ester pyridinium intermediate. This intermediate was further reacted with tetrabutyl ammonium hydrogen sulfate to provide tetrabutyl ammonium salt (2S, 5R)-6-sulfooxy-2-(tert-butoxy carbonyl aminomethyl)-7-oxo-1, 6-diaza-bicyclo[3.2.1]octane (VIII).

The compound of the Formula (VIII) was dissolved in a suitable solvent such as 10% tetrahydrofuran:water mixture and was passed through the column packed with Dowex 50WX8 200 Na$^+$ resin to provide sodium salt of (2S, 5R)-6-sulfoxy-2-(tert-butoxy carbonyl aminomethyl)-7-oxo-1, 6-diaza-bicyclo[3.2.1]octane (IX).

Scheme 1

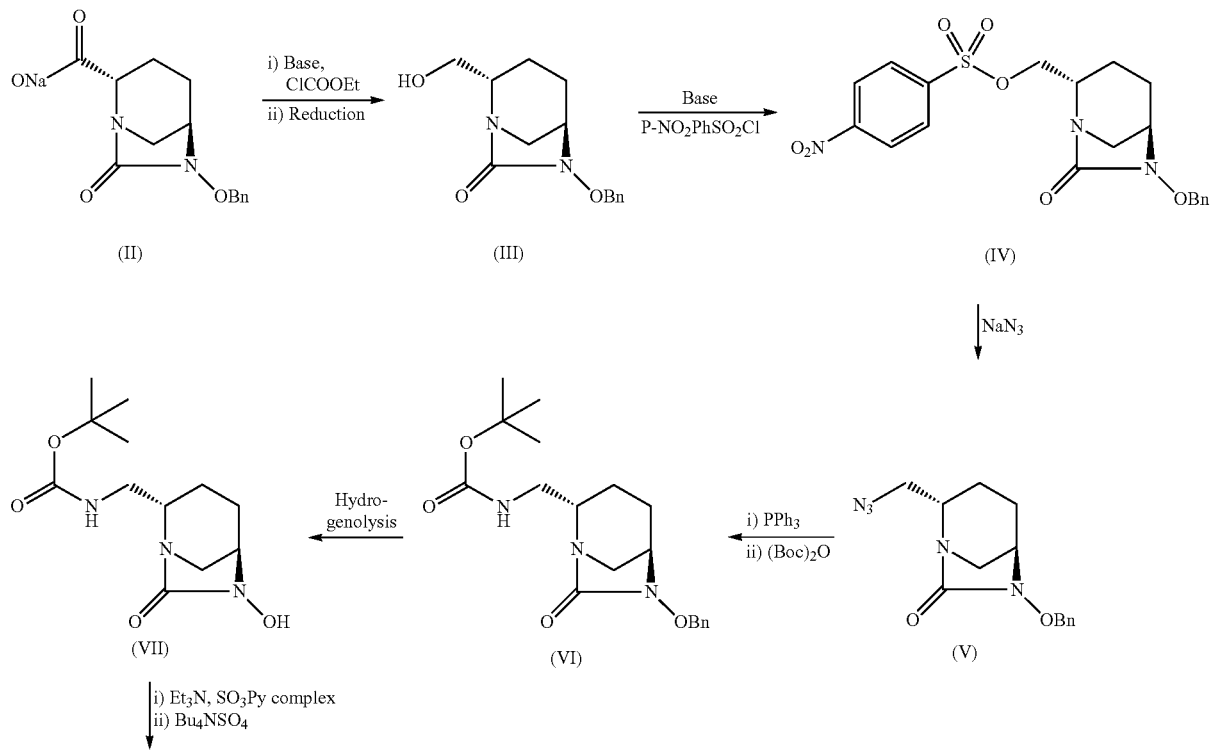

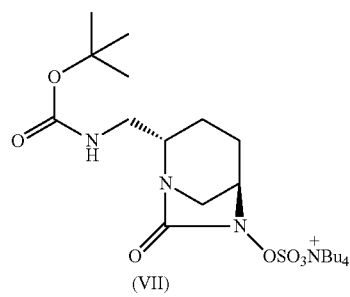
(VII)

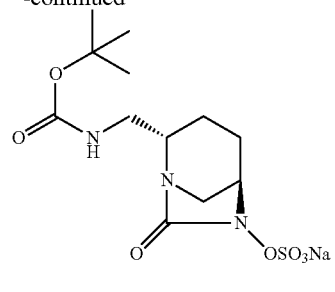
(IX)

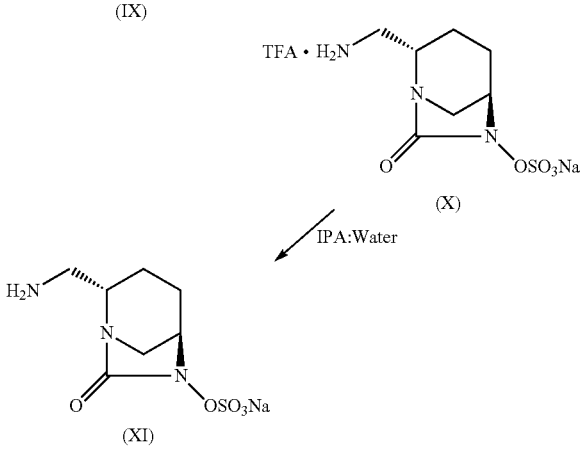
(X)

(XI)

The compound of Formula (IX) was reacted with trifluoroacetic acid in a suitable solvent such as dichloromethane to provide trifluoroacetic acid and sodium salt of 6-sulfooxy-2-(amino methyl)-7-oxo-1,6-diazabicyclo[3.2.1]octane (X). This trifluoroacetic acid and sodium salt (X) was further treated with water isopropyl alcohol mixture to obtain zwitterion form, (2S, 5R)-6-sulfooxy-2-(aminomethyl)-7-oxo-1,6-diaza-bicyclo[3.2.1]octane (XI).

In some embodiments, there is provided a process for the preparation of (2S, 5R)-6-sulfooxy-2-(aminomethyl)-7-oxo-1,6-diaza-bicyclo[3.2.1]octane of Formula (XI), comprising:

(Formula XI)

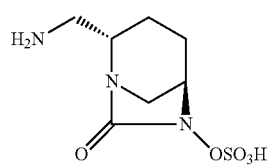

(a) Reacting a compound of Formula (II) with ethyl chloroformate in presence of N-methyl morpholine followed by treating with sodium borohydride to obtain a compound of Formula (III);

(Formula II)

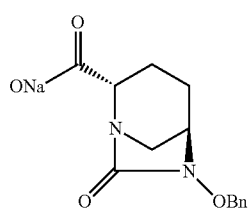

(Formula III)

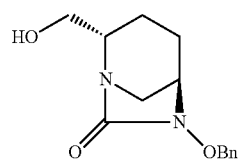

(b) Reacting a compound of Formula (III) with p-nitrophenyl sulfonyl chloride in presence of triethylamine to obtain a compound of Formula (IV);

(Formula IV)

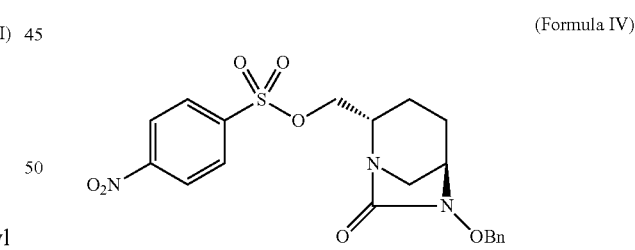

(c) Reacting a compound of Formula (IV) with sodium azide to obtain a compound of Formula (V);

(Formula V)

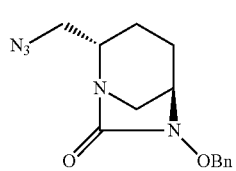

(d) Reacting a compound of Formula (V) with triphenylphosphine, followed by treating with di-tert-butyl dicarbonate to obtain a compound of Formula (VI);

(Formula VI)

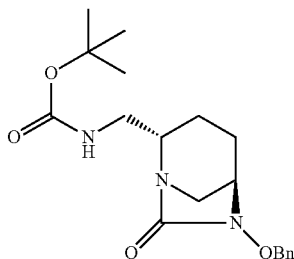

(e) Hydrogenolysis of a compound of Formula (VI) in presence of palladium on carbon catalyst and hydrogen gas to obtain a compound of Formula (VII);

(Formula VII)

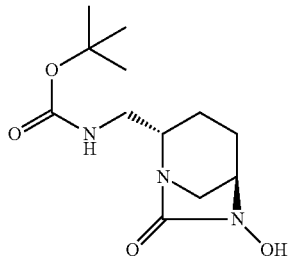

(f) Reacting a compound of Formula (VII) with sulfur trioxide-pyridine complex, followed by a reaction with tetrabutyl ammonium hydrogen sulfate to obtain a compound of Formula (VIII);

(Formula VIII)

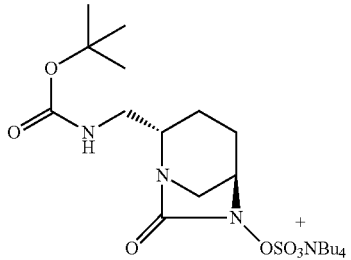

(g) Passing a solution of a compound of Formula (VIII) through a column packed with sodium resin to obtain a compound of Formula (IX);

(Formula IX)

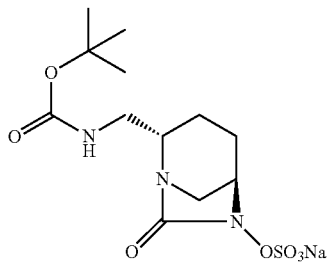

(h) Reacting a compound of Formula (IX) with trifluoroacetic acid in suitable solvent to obtain a compound of Formula (X); and (Formula X)

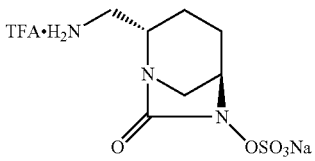

(i) Converting a compound of Formula (X) to a compound of Formula (XI) by treating with water isopropyl mixture.

In some embodiments, there are provided pharmaceutical compositions comprising a compound of Formula (I) or a stereoisomer or a pharmaceutically acceptable derivative thereof.

In some embodiments, there is provided a compound of Formula (X) having purity of more than 97% as determined by HPLC. In some embodiments, there is provided a pharmaceutical composition comprising a compound of Formula (X) having purity more than 97% as determined by HPLC. In some embodiments, there is provided a compound of Formula (XI) having purity of more than 99% as determined by HPLC. In some embodiments, there is provided a pharmaceutical composition comprising a compound of Formula (XI) having purity more than 99% as determined by HPLC.

In some other embodiments, there is provided a method for preventing or treating bacterial infection in a subject, said method comprising administering to said subject a pharmaceutically effective amount of a compound of Formula (I) or a stereoisomer or a pharmaceutically acceptable derivative thereof. In some embodiments, there is provided a method for preventing or treating a bacterial infection in a subject, said infection being caused by bacteria producing one or more beta-lactamase enzymes, said method comprising administering to said subject a pharmaceutically effective amount of a compound of Formula (I) or a stereoisomer or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable derivative thereof. In some other embodiments, there is provided a method for preventing or treating bacterial infection in a subject, said infection being caused by bacteria producing one or more beta-lactamase enzymes, said method comprising administering to said subject a pharmaceutically effective amount of a pharmaceutical composition comprising a compound of Formula (I) or a stereoisomer or a pharmaceutically acceptable derivative thereof.

In some embodiments, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof. In some other embodiments, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof. In some other embodiments, there are provided pharmaceutical compositions comprising: (a) a compound of Formula (I) or a stereoisomer or a pharmaceutically acceptable derivative thereof, (b) at least one beta-lactamase inhibitor or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I) or a stereoisomer or a pharmaceutically acceptable derivative thereof, and (b) at least one beta-lactamase inhibitor or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I) or a stereoisomer or a pharmaceutically acceptable derivative thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I) or a stereoisomer or a pharmaceutically acceptable derivative thereof, (b) at least one beta-lactamase inhibitor or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable derivative thereof, and (b) at least one beta-lactamase inhibitor or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I) or a stereoisomer or a pharmaceutically acceptable derivative thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I) or a stereoisomer or a pharmaceutically acceptable derivative thereof, (b) at least one beta-lactamase inhibitor or a pharmaceutically acceptable derivative thereof, and (c) at least one antibacterial agent or a pharmaceutically acceptable derivative thereof.

In some embodiments, there is provided a method for preventing or treating bacterial infection in a subject, said infection being caused by bacteria producing one or more beta-lactamase enzymes, said method comprising administering to said subject a pharmaceutically effective amount of a compound according to invention, or combination of a compound according to invention with at least one beta-lactamase inhibitor, or combination of a compound according to invention with at least one antibacterial agent, or combination of a compound according to invention with at least one beta-lactamase inhibitor and at least one antibacterial agent. In some embodiments, there is provided a method for preventing or treating bacterial infection in a subject, said infection being caused by bacteria producing one or more beta-lactamase enzymes, said method comprising administering to said subject a pharmaceutically effective amount of a pharmaceutical composition according to present invention.

In some embodiments, there are provided pharmaceutical compositions comprising: (a) (2S, 5R)-6-sulfooxy-2-(aminomethyl)-7-oxo-1,6-diaza-bicyclo[3.2.1] octane or a stereoisomer or a pharmaceutically acceptable derivative thereof, and (b) Sulbactam or a pharmaceutically acceptable derivative thereof.

In some other embodiments, there is provided a method for preventing or treating bacterial infection in a subject, said method comprising administering to said subject a pharmaceutically effective amount of: (a) (2S, 5R)-6-sulfooxy-2-(aminomethyl)-7-oxo-1,6-diaza-bicyclo[3.2.1] octane or a stereoisomer or a pharmaceutically acceptable derivative thereof, and (b) Sulbactam or a pharmaceutically acceptable derivative thereof.

In some other embodiments, there is provided a method for preventing or treating bacterial infection in a subject, said infection being caused by bacteria producing one or more beta-lactamase enzymes, said method comprising administering to said subject a pharmaceutically effective amount of: (a) (2S, 5R)-6-sulfooxy-2-(aminomethyl)-7-oxo-1,6-diaza-bicyclo[3.2.1] octane or a stereoisomer or a pharmaceutically acceptable derivative thereof, and (b) Sulbactam or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) (2S, 5R)-6-sulfooxy-2-(aminomethyl)-7-oxo-1,6-diaza-bicyclo[3.2.1] octane or a stereoisomer or a pharmaceutically acceptable derivative thereof, and (b) Sulbactam or a pharmaceutically acceptable derivative thereof.

In some embodiments, there is provided a method for preventing or treating bacterial infection in a subject, said infection being caused by bacteria producing one or more beta-lactamase enzymes, said method comprising administering to said subject a pharmaceutically effective amount of a pharmaceutical composition comprising: (a) (2S, 5R)-6-sulfooxy-2-(aminomethyl)-7-oxo-1,6-diaza-bicyclo[3.2.1] octane or a stereoisomer or a pharmaceutically acceptable derivative thereof, and (b) Sulbactam or a pharmaceutically acceptable derivative thereof.

In some embodiments, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable derivative thereof.

In some embodiments, the compositions and methods according to the invention use compounds of Formula (I) or a stereoisomer or a pharmaceutically acceptable derivative thereof in combination with at least one antibacterial agent. A wide variety of antibacterial agents can be used. Typical, non-limiting examples of antibacterial agents include one or more of antibacterial compounds generally classified as Aminoglycosides, Ansamycins, Carbacephems, Cephalosporins, Cephamycins, Lincosamides, Lipopeptides, Macrolides, Monobactams, Nitrofurans, Penicillins, Polypeptides, Quinolones, Sulfonamides, Tetracyclines, Oxazolidinone and the like.

Typical, non-limiting examples of Aminoglycoside antibacterial agents include Amikacin, Gentamicin, Kanamycin, Neomycin, Netilmicin, Tobramycin, Paromomycin, Arbekacin, Streptomycin, Apramycin and the like. Typical, non-limiting examples of Ansamycin antibacterial agents include Geldanamycin, Herbimycin and the like. Typical, non-limiting examples of Carbacephem antibacterial agents include Loracarbef and the like. Typical, non-limiting examples of Carbapenam antibacterial agents include Ertapenem, Doripenem, Imipenem, Meropenem and the like.

Typical, non-limiting examples of Cephalosporin and Cephamycin antibacterial agents include Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cephamycin, Cefoxitin, Cefotetan, Cefmetazole, Carbacephem, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Cefiolene, Ceftizoxime, Oxacephem, Cefepime, Cefozopran, Cefpirome, Cefquinome, Ceftobiprole, Cetiofur, Cefquinome, Cefovecin, CXA-101, Ceftaroline, Ceftobiprole, Cefoselis, Cefluprenam, Cefclidin, Loracarbacef, Ceftolozane, Latamoxef and the like.

Typical, non-limiting examples of Lincosamide antibacterial agents include Clindamycin, Lincomycin and the like. Typical, non-limiting examples of Macrolide antibacterial agents include Azithromycin, Clarithromycin, Dirithromycin, Erythromycin, Roxithromycin, Troleandomycin, Telithromycin, Spectinomycin and the like. Typical, non-limiting examples of Monobactam antibacterial agents include Aztreonam and the like. Typical, non-limiting examples of Nitrofuran antibacterial agents include Furazolidone, Nitrofurantoin and the like. Typical, non-limiting examples of Penicillin antibacterial agents include Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Colistin, Polymyxin B and the like.

Typical, non-limiting examples of Polypeptide antibacterial agents include Bacitracin, Colistin, Polymyxin B and the like. Typical, non-limiting examples of Quinolone antibacterial agents include Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin and the like. Typical, non-limiting examples of Sulfonamide antibacterial agents include Mafenide, Sulfonamidochrysoidine, Sulfacetamide, Sulfadiazine, Sulfamethizole, Sulfamethoxazole, Sulfasalazine, Sulfisoxazole, Trimethoprim and the like.

Typical, non-limiting examples of Tetracycline antibacterial agents include Demeclocycline, Doxycycline, Minocycline, Oxytetracycline, Tetracycline, Tigecycline and the like. Typical, non-limiting examples of Oxazolidinone anti bacterial agents include Linezolid, Ranbezolid, Torezolid, Radezolid and the like. Typical, non-limiting examples of beta-lactamase inhibitors include Sulbactam, Tazobactam or Clavulanic acid and the like.

The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, preservatives, stabilizing agents, binding agents and the like.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water. In some other embodiments, the pharmaceutical compositions according to the invention are in the form of a frozen composition that can be diluted with a compatible diluent prior to parenteral administration. In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition, nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered separately, the invention further provides for combining separate pharmaceutical compositions in kit form. The kit may comprise one or more separate pharmaceutical compositions, each comprising one or more active ingredients. Each of such separate compositions may be present in a separate container such as bottle, vial, syringes, boxes, bags, and the like. Typically, the kit comprises directions for the administration of the separate components. The kit form is particularly advantageous when the separate components are preferably administered in different dosage intervals. When the active ingredients are administered separately, they may be administered simultaneously or one after the other.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and methods disclosed herein are useful in preventing or treating bacterial infections. Advantageously, the compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intra-abdominal infections, respiratory tract infections, pneumonia (nosocomial), bacteremia meningitis, surgical, infections and the like.

Surprisingly, the compounds, compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibacterial agents represents a significant improvement in the art.

In general, the compounds of Formula (I) or a stereoisomer or pharmaceutically acceptable derivative thereof according to invention are also useful in increasing antibacterial effectiveness of an antibacterial agent in a subject. The antibacterial effectiveness of one or more antibacterial gents may be increased, for example, by co-administering said antibacterial agents or a pharmaceutically acceptable derivative thereof with a pharmaceutically effective amount of a compound of Formula (I) or a stereoisomer or a pharmaceutically acceptable derivative thereof according to the invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Synthesis of (2S, 5R)-6-sulfooxy-2-(aminomethyl)-7-oxo-1, 6-diaza-bicyclo [3.2.1]octane (XI)

Step 1: Preparation of (2S, 5R)-6-(benzyloxy)-2-(hydroxymethyl)-7-oxo-1, 6-diaza-bicyclo[3.2.1]octane (III)

The sodium salt of (2S, 5R)-6-benzyloxy-7-oxo-1, 6-diaza-bicyclo [3.2.1] octane-2-carboxylic acid (II) (50 g, 0.16 moles, prepared as per the procedure described in Indian Patent Application No. 699/MUM/2013) was suspended in tetrahydrofuran (500 ml). To the suspension was added N-methyl morpholine (18.4 ml, 0.16 moles) under stirring. The reaction mixture was cooled to about −10° C. and ethyl chloroformate was added via addition funnel and stirred for 1 hour at about −10° C. To the reaction mixture was added $NaBH_4$ (9.56 g, 0.25 moles) in lots under stirring. The reaction was monitored with the help of thin layer chromatography (TLC). After completion of reaction, water (500 ml) followed by ethyl acetate (500 ml) was added to the reaction mass. The reaction mixture was stirred for 30 minutes and the layers were separated. Organic layer was washed with brine (200 ml). The solvent was evaporated under vacuum to dryness to provide 43 g of (2S, 5R)-6-(benzyloxy)-2-(hydroxymethyl)-7-oxo-1,6-diaza-bicyclo [3.2.1] octane (III) as a pale yellow oil (99% yield).

Analysis:
Mass: 263.2 [M+1]; for Molecular Formula: $C_{14}H_{18}N_2O_3$; and Molecular Weight: 262.3.
$^1$H NMR (CDCl$_3$): δ 7.28-7.49 (m, 5H), 4.96 (dd, 2H), 4.10-4.16 (m, 1H), 3.60-3.74 (m, 3H), 3.55-3.59 (m, 2H), 1.92-2.02 (m, 2H), 1.54-1.58 (m, 2H), 1.36-1.41 (m, 1H).

Step 2: Preparation of (2S, 5R)-6-(benzyloxy)-2-(4-nitrophenyl sulfonyloxy-methyl)-7-oxo-1, 6-diaza-bicyclo[3.2.1]octane (IV)

Solution of (2S, 5R)-6-(benzyloxy)-2-(hydroxymethyl)-7-oxo-1, 6-diaza-bicyclo [3.2.1] octane (24 g, 0.091 moles) in dichloromethane (240 ml) was cooled to about 10° C. To the above solution, triethylamine (38.2 ml, 0.274 moles) followed by p-nitrophenylsulfonyl chloride were added. This reaction mixture was stirred for 2 hours at the same temperature and then quenched with water (200 ml). The reaction mixture was stirred for 15 minutes and the layers were separated. Organic layer was washed with brine (200 ml). The solvent was evaporated under vacuum to yield 35.3 g of (2S, 5R)-2-(4-nitrophenyl sulfonyloxy-methyl)-6-(benzyloxy)-7-oxo-1,6-diaza-bicyclo [3.2.1] octane (IV) as a pale yellow solid, (85% yield).

Analysis:
Mass: 448.2 [M+1]; for Molecular Formula: $C_{20}H_{21}N_3O_7S$ and Molecular Weight: 447.5.
$^1$H NMR (CDCl$_3$): δ 8.39 (d, 2H), 8.11 (d, 2H), 7.35-7.40 (m, 5H), 5.00 (dd, 2H), 3.73-4.21 (m, 2H), 3.33 (m, 1H), 2.98-3.16 (m, 3H), 1.70-2.00 (m, 2H), 1.51-1.61 (m, 2H).

Step 3: Preparation of (2S, 5R)-6-(benzyloxy)-2-(azidomethyl)-7-oxo-1, 6-diaza-bicyclo [3.2.1] octane (V)

To a solution of (2S, 5R)-6-(benzyloxy)-2-(4-nitrophenyl sulfonyloxy-methyl)-6-oxo-1,6-diaza-bicyclo [3.2.1] octane (30 g, 0.067 moles) in N, N-dimethyl formamide (150 ml), was added NaN$_3$ (8.7 g, 0.134 moles) and reaction mixture was heated at about 65° C. for 4 hours. After completion of reaction on TLC, the reaction mixture was cooled to about 25° to 30° C., and water (750 ml) followed by ethyl acetate (300 ml) were added. The reaction mass was stirred for 15 minutes. The organic layer was separated and washed with water (200 ml) followed by brine (200 ml). The solvent was evaporated under vacuum to provide 14 g of (2S, 5R)-2-(azidomethyl)-6-(benzyloxy)-7-oxo-1,6-diaza-bicyclo [3.2.1] octane (V) as a solid, (72% yield).

Analysis:
Mass: 288.1 [M+1]; for Molecular Formula: $C_{14}H_{17}N_5O_2$; and Molecular Weight: 287.3.
$^1$H NMR (CDCl$_3$): δ 7.28-7.42 (m, 5H), 4.94 (dd, 2H), 3.48-3.57 (m, 2H), 3.29-3.33 (m, 2H), 2.92 (d, 2H), 1.93-2.02 (m, 2H), 1.41-1.59 (m, 2H).

Step 4: Preparation of (2S, 5R)-6-benzyloxy-2-(tert-butoxycarbonylaminomethyl)-7-oxo-1, 6-diaza-bicyclo [3.2.1] octane (VI)

To a solution of (2S, 5R)-6-(benzyloxy)-2-(azidomethyl)-7-oxo-1, 6-diaza-bicyclo[3.2.1] octane (13 g, 0.045 moles) in tetrahydrofuran (130 ml), was added triphenylposphine (23.7 g, 0.19 moles) and reaction mixture was stirred for 12 hours at about 25-30° C. To the reaction mixture, water (1 ml) was added and it was stirred for 2 hours at about 25-30° C. After 2 hours, triethylamine (19 ml, 0.135 moles) followed by di-tert-butylpyrocarbonate (20.5 ml, 0.95 moles) were added and the mixture was stirred for 4 hours at about 25-30° C. After completion of reaction monitored by TLC, water (130 ml) followed by ethyl acetate (130 ml) were added, and the reaction mass was stirred for 15 minutes. The organic layer was separated and washed with brine (200 ml). The solvent was evaporated under vacuum and the residue was purified by using silica gel (60-120 mesh) column chromatography by using a mixture of ethyl acetate:hexane (2:8) to provide 8 g of (2S, 5R)-6-benzylozy-2-(tert-butoxycarbonylaminomethyl)-7-oxo-1,6-diaza-bicyclo [3.2.1] octane (VI) as solid, (49% yield).

Analysis:
Mass: 362.1 [M+1]; for Molecular Formula: $C_{19}H_{27}N_3O_4$ and Molecular Weight: 361.4.
$^1$H NMR (CDCl$_3$): δ 7.28-7.45 (m, 5H), 5.03 (d, 1H), 4.97 (bs, 1H), 4.89 (d, 1H), 3.43-3.46 (m, 1H), 3.26-3.36 (m, 3H), 2.84-2.96 (m, 2H), 1.94-2.04 (m, 3H), 1.57-1.61 (m, 1H), 1.42 (s, 9H).

Step 5: Preparation of (2S, 5R)-6-hydroxy-2-(tert-butoxycarbonylaminomethyl)-7-oxo-1, 6-diaza-bicyclo [3.2.1] octane (VII)

To a solution of (2S, 5R)-6-benzylozy-2-(tert-butoxycarbonylaminomethyl)-7-oxo-1,6-diaza-bicyclo[3.2.1]octane (8 g, 0.022 moles) in methanol (60 ml), was added 10% palladium on charcoal and the mixture was hydrogenated under 60 psi pressure of hydrogen gas for 3 hours at about 25-30° C. The reaction mixture was filtered through celite bed filter to remove the catalyst and the filtrate was concentrated under vacuum to obtain 6 g of (2S, 5R)-6-hydroxy-2-(tert-butoxycarbonylaminomethyl)-7-oxo-1,6-diaza-bicyclo [3.2.1] octane (VII) as white solid, (100% yield).

Analysis:
Mass: 272.1 [M+1]; for Molecular Formula: $C_{12}H_{21}N_3O_4$; and Molecular Weight: 271.3.
$^1$H NMR (CDCl$_3$): δ 4.92 (bs, 1H), 3.29-3.73 (m, 3H), 2.75-2.98 (m, 2H), 2.35-2.65 (m, 3H), 1.96-2.02 (m, 2H), 1.67-1.73 (m, 1H), 1.47 (s, 9H).

Step 6: Preparation of Tetrabutylammonium salt of (2S, 5R)-6-sulfooxy-2-(tert-butoxycarbonylaminomethyl)-7-oxo-1, 6-diaza-bicyclo [3.2.1] octane (VIII)

To a solution of (2S, 5R)-6-hydroxy-2-(tert-butoxycarbonylaminomethyl)-7-oxo-1,6-diaza-bicyclo[3.2.1]octane (6 g, 0.022 moles) in dichloromethane (60 ml) under argon atmosphere, was added triethylamine (9.2 ml, 0.066 moles) followed by sulfur trioxide-pyridine complex (7 g, 0.044 moles) under stirring at about 30° C. The reaction mixture was stirred for 2 hours and then poured into 0.5 N potassium dihydrogen phosphate buffer solution (120 ml). Organic layer was separated and discarded. To the aqueous layer solid tetrabutylammonium hydrogen sulfate (6.75 g, 0.0.19 moles) was added and stirred for 2 hours at about 30° C. The reaction mixture was extracted with dichloromethane (60 ml×2). The layers were separated. The combined organic layer was evaporated under vacuum below 40° C. to provide 10 g of tetrabutylammonium salt of (2S, 5R)-6-sulfooxy-2-(tert-butoxycarbonylaminomethyl)-7-oxo-1,6-diaza-bicyclo [3.2.1]octane (VIII) as a white solid, (87% yield).

Analysis:
Mass: (M−1): 350.1 as a free sulfonic acid; for Molecular Formula: $C_{12}H_{21}N_3O_7S.N(C_4H_9)_4$; and Molecular Weight: 592.9.
$^1$H NMR (CDCl$_3$): δ 4.94 (bs, 1H), 3.28-3.37 (m, 11H), 2.72-2.95 (m, 3H), 2.32-2.64 (m, 3H), 1.62-1.78 (m, 11H), 1.40-1.49 (m, 16H), 0.98-1.02 (m, 12H).

Step 7: Preparation of Sodium salt of (2S, 5R)-6-sulfooxy-2-(tert-butoxycarbonyl aminomethyl)-7-oxo-1, 6-diaza-bicyclo[3.2.1]octane (IX)

The tetrabutylammonium salt of (2S, 5R)-6-sulfooxy-2-(tert-butoxycarbonyl aminomethyl)-7-oxo-1,6-diaza-bicyclo[3.2.1]octane (9 g) was dissolved in 10% tetrahydrofuran: water and the solution was passed through column (45 cm length and 2.0 cm diameter) packed with Dowex 50WX8 200 Na$^+$ resin. The column was eluted with 10% tetrahydrofuran: water mixture (250 ml). The combined fractions having compound were evaporated under vacuum (4 mm Hg) to obtain 2.9 g of sodium salt of (2S, 5R)-6-sulfooxy-2-(tert-butoxycarbonyl aminomethyl)-7-oxo-1,6-diaza-bicyclo[3.2.1]octane (IX) as white solid, (72% yield). The intermediate was used for next reaction.

Analysis:
Mass: (M−1): 373.1 as a free sulfonic acid; for Molecular Formula: $C_{12}H_{20}N_3O_7SNa$; and Molecular Weight: 374.74.

Step 8: Preparation of Sodium and trifluoroacetate salt of (2S, 5R)-6-sulfooxy-2-(aminomethyl)-7-oxo-1, 6-diaza-bicyclo[3.2.1]octane (X)

The sodium salt of (2S, 5R)-6-sulfooxy-2-(tert-butoxycarbonylaminomethyl)-7-oxo-1,6-diaza-bicyclo[3.2.1]octane (2.4 g, 0.006 moles) was suspended in dichloromethane (6 ml) and to the reaction mixture was slowly added trifluoroacetic acid (6 ml) at about 0-5° C. The reaction mixture was stirred between about 0-5° C. for additional 2 hours. The solvent and excess trifluoroacetic acid was evaporated under vacuum below 40° C. to approximately ⅓ of its original volume to provide pale yellow oily residue. This oily residue was triturated with diethyl ether and ether was decanted (40 ml×2). The crude solid was again triturated with dichloromethane (40 ml×2) and solvents were decanted. The final solid was dried under vacuum below 40° C. to furnish 2.2 g of sodium and trifluoroacetic acid salt of (2S, 5R)-6-sulfooxy-2-(aminomethyl)-7-oxo-1,6-diaza-bicyclo [3.2.1]octane (X) (90% yield).

Analysis:

Mass: (M−1): 250.1 as a free sulfonic acid; for Molecular Formula: $C_7H_{13}N_3O_5SNa\ CF_3COO$; and Molecular Weight: 387.26.

$^1H$ NMR (DMSO-d6): δ 7.82 (br s, 3H), 4.00 (d, 1H), 3.35-3.40 (m, 3H), 2.28-2.91 (m, 2H), 1.74-1.79 (m, 3H), 1.44-1.47 (m, 1H); and Purity as determined by HPLC: 97.64%.

Step 9: Preparation of (2S, 5R)-6-sulfooxy-2-(aminomethyl)-7-oxo-1,6-diaza-bicyclo[3.2.1] octane (XI)

Sodium and trifluoroacetic acid salt of (2S, 5R)-6-sulfooxy-2-(aminomethyl)-7-oxo 1,6-diaza-bicyclo[3.2.1]octane (2 g, 0.005 moles) was dissolved in distilled water (2 ml) and to the clear solution, was slowly added isopropyl alcohol (14 ml) at about 25° C. The reaction mixture was stirred for 12 hours. The precipitate was filtered under suction to provide a solid, which was dried under vacuum below 40° C. to furnish 1.2 g of (2S, 5R)-6-sulfooxy-2-(aminomethyl)-7-oxo-1,6-diaza-bicyclo[3.2.1]octane (XI) (92% yield).

Analysis:

Mass: 252 (M+1), 250 (M−1); for Molecular Formula: $C_7H_{14}N_3O_5S$; and Molecular Weight: 251.3.

$^1H$ NMR (DMSO-d6): δ 7.78 (br s, 3H), 4.24 (s, 1H), 3.62-3.65 (m, 1H), 3.20-3.42 (m, 4H), 2.00-2.18 (m, 2H), 1.81-1.98 (m, 1H), 1.60-1.65 (m, 1H);

$^{13}C$ NMR ($D_2O$): 18, 20, 40, 43, 56, 60, 171; and

Purity as determined by HPLC: 99.77%.

Biological Activity Data

The biological activity of representative compounds according to the invention against various bacterial strains was investigated. In a typical study, overnight grown bacterial cultures were diluted appropriately and inoculated on the agar media containing doubling dilutions of the test compounds. Observations for growth or no growth was performed after 16-20 hours of incubation at 35±2° C. in the ambient air. The overall procedure was performed as per Clinical and Laboratory Standards Institute (CLSI) recommendations (Clinical and Laboratory Standards Institute (CLSI), Performance Standards for Antimicrobial Susceptibility Testing, 20th Informational Supplement, M 100-S20, Volume 30, No. 1, 2010). The results of these studies are summarized in Table 1 and 2, wherein the antibacterial activity is expressed as minimum inhibitory concentration (MIC). Table 1 shows the antibacterial activity profile of (2S, 5R)-6-sulfooxy-2-(aminomethyl)-7-oxo-1,6-diaza-bicyclo[3.2.1]octane (Compound XI) in comparison to known antibacterial agents. The Compound (XI), which is the free zwitterionic form of Compound (X), was also studied for the antibacterial activity profile. The Compound (XI) exhibits good antibacterial activity against resistant ESBL strains of K. pneumoniae, E. coli and P. aeruginosa. The activity profile of the Compound (XI) was found to be better than Ceftazidime and Cefepime against all tested strains. The Compound (XI) also exhibited better activity than Imipenem against resistant ESBL strains K. pneumoniae and P. aeruginosa.

The antibacterial activity of the Compound (XI) was also studied in combination with other beta-lactam antibacterial agents. Data in Table 2 shows the results of the ESBL enzyme inhibition in presence of Compound (XI) in combination with Ceftazidime. Results obtained using Ceftazidime alone were used as control. The antibacterial activity of the combination of Compound (XI) (4 µg/ml) and Ceftazidime was compared with (i) combination of Cetftazidime and Avibactam (4 µg/ml); and (ii) Imipenem alone. The results showed that the combination of the Compound (XI) and Ceftazidime exhibited good antibacterial activity against resistant bacterial strains. The presence of Compound (XI) in combination with Ceftazidime significantly lowered the MIC values of Ceftazidime alone. From the results in Table 2, it appears that the combination comprising Compound (XI) and Ceftazidime exhibited synergism and showed potent antibacterial inhibition against those resistant bacterial strains where Ceftazidime alone was found to be ineffective.

TABLE 1

Antibacterial Activity of the (2S, 5R)-6-sulfooxy-2-(aminomethyl)-7-oxo-1,6-diaza-bicyclo[3.2.1]octane (Compound XI) in comparison with other antibacterial agents.

| | | | MIC (µg/ml) | | | |
|---|---|---|---|---|---|---|
| Sr. | Organism (Strain) | ESBL | Cefta-zidime | Cefe-pime | Imi-penem | Compound (XI) |
| 1. | E. coli (NCTC 13353) | CTXM-15 | >32 | >32 | 0.25 | 1 |
| 2. | E. coli (NCTC 13352) | TEM 10 | >32 | 2 | 0.25 | 2 |
| 3. | K. pneumoniae (H521) | KPC | >32 | >32 | 16 | 1 |
| 4. | E. coli (7MP) | SHV, CMY | >32 | 16 | 1 | 4 |
| 5. | K. pneumoniae (S48) | NDM, SHV | >32 | >32 | 16 | 1 |
| 6. | P. aeruginosa (MBL18) | VIM | >32 | >32 | 16 | 8 |

TABLE 2

Antibacterial Activity of (2S, 5R)-6-sulfooxy-2-(aminomethyl)-7-oxo -1,6-diaza-bicyclo [3.2.1]octane (Compound XI) in combination with Ceftazidime.

| | | | MIC (µg/ml) | | | |
|---|---|---|---|---|---|---|
| | | | Ceftazidime | | | |
| Sr. | Strains | ESBL | Control | + Compound (XI) (4 µg/ml) | + Avi-bactam (4 µg/ml) | Imi-penem |
| 1. | K. pneumoniae ATCC 700603 | SHV-18 | 16 | 0.03 | 0.5 | 0.12 |
| 2. | E. coli H483 | CMY-2 | >32 | ≤0.015 | 1 | 0.25 |
| 3. | K. pneumoniae J101 | TEM-1, SHV-12, OMP | >32 | 2 | 1 | 2 |
| 4. | K. pneumoniae J102 | TEM-1, SHV-5, OMP | >32 | 4 | 0.5 | 8 |

The invention claimed is:
1. A compound of Formula (I):

Formula (I)

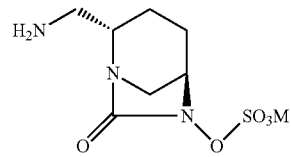

or a stereoisomer or a pharmaceutically acceptable derivative thereof; wherein M is a cation.

2. The compound according to claim 1, wherein M is hydrogen, sodium or potassium.

3. The compound according to claim 1, which is (2S, 5R)-6-sulfooxy-2-(aminomethyl)-7-oxo-1,6-diaza-bicyclo [3.2.1]octane or a stereoisomer or a pharmaceutically acceptable derivative thereof.

4. A pharmaceutical composition for treating bacterial infection, wherein the composition comprises a compound according to claim 1.

5. The pharmaceutical composition according to claim 4, further comprising at least one beta-lactamase inhibitor or a pharmaceutically acceptable derivative thereof.

6. The pharmaceutical composition according to claim 4, further comprising at least one antibacterial agent or a pharmaceutically acceptable derivative thereof.

7. The pharmaceutical composition according to claim 6, further comprising at least one beta-lactamase inhibitor or a pharmaceutically acceptable derivative thereof.

8. The pharmaceutical composition according to claim 5, wherein the beta-lactamase inhibitor is selected from the group consisting of Sulbactam, Tazobactam, Clavulanic acid, and pharmaceutically acceptable derivatives thereof.

9. The pharmaceutical composition according to claim 6, wherein at least one antibacterial agent is selected from a group consisting of Aminoglycosides, Ansamycins, Carbacephems, Cephalosporins, Cephamycins, Lincosamides, Lipopepetides, Macrolidees, Monobactams, Nitrofuran, Penems, Carbapenems, Penicillins, Polypeptide, Quinolones, Sulfonamides, Tetracyclines, and Oxazolidinone antibacterial agents.

10. The pharmaceutical composition according to claim 6, wherein at least one antibacterial agent is a beta lactam antibacterial agent.

11. The pharmaceutical composition according to claim 6, wherein at least one antibacterial agent is a cephalosporin antibiotic selected from the group consisting of Cephalotin, Cephaloridine, Cefaclor, Cefadroxil, Cefamandole, Cefazolin, Cefalexin, Cefradine, Ceftizoxime, Cefoxitin, Cephacetrile, Cefotiam, Cefotaxime, Cefsulodin, Cefoperazone, Cefmenoxime, Cefmetazole, Cepfaloglycin, Cefonicid, Cefodizime, Cefpirome, Ceftazidime, Ceftriaxone, Cefpiramide, Cefbuperazone, Cefozopran, Cefepime, Cefoselis, Cefluprenam, Cefuzonam, Cefpimizole, Cefclidin, Cefixime, Ceftibuten, Cefdinir, Cefpodoxime auxetil, Cefpodoxime proxetil, Cefteram pivoxil, Cefetamet pivoxil, Cefcapene pivoxil, Cefditoren pivoxel, Cefuroxime, Cefuroxime auxetil, Loracarbacef, Ceftaroline, Ceftolozane, and Latamoxef.

12. The pharmaceutical composition according to claim 6, wherein the antibacterial agent is selected from the group consisting of Cetazidime, Cefepime, Cefpirome, Piperacillin, Ertapenem, Doripenem, Meropenem, Imipenem, Ceftraroline, and Ceftolozane.

13. The pharmaceutical composition according to claim 5, comprising (a) (2S, 5R)-6-sulfooxy-2-(aminomethyl)-7-oxo-1,6-diaza-bicyclo [3.2.1]octane or a stereoisomer or a pharmaceutically acceptable derivative thereof, and (b) Sulbactam or a pharmaceutically acceptable derivative thereof.

14. A process for preparation of (2S, 5R)-6-sulfooxy-2-(aminomethyl)-7-oxo-1,6-diaza-bicyclo [3.2.1]octane of Formula (XI), wherein the process comprising:

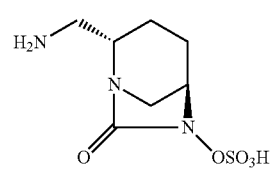
(Formula XI)

(a) Converting a compound of Formula (II) to a compound of Formula (III);

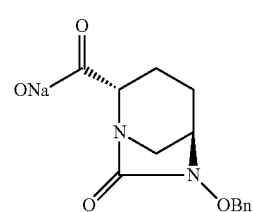
(Formula II)

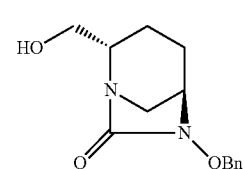
(Formula III)

(b) Reacting a compound of Formula (III) with p-nitrophenyl sulfonyl chloride in presence of a base to obtain a compound of Formula (IV);

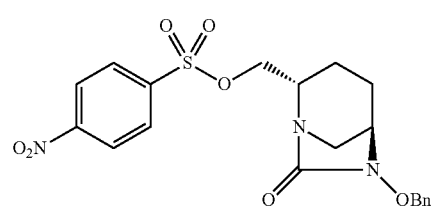
(Formula IV)

(c) Reacting a compound of Formula (IV) with sodium azide to obtain a compound of Formula (V);

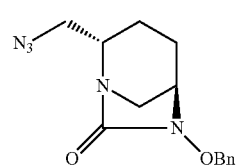
(Formula V)

(d) Converting a compound of Formula (V) to a compound of Formula (VI);

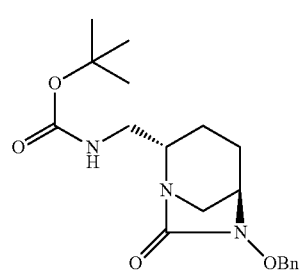
(Formula VI)

(e) Hydrogenolysis of a compound of Formula (VI) to obtain a compound of Formula (VII);

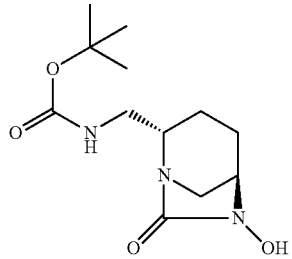
(Formula VII)

(f) Reacting a compound of Formula (VII) with sulfonating agent, followed by a reaction with tetrabutyl ammonium hydrogen sulfate to obtain a compound of Formula (VIII);

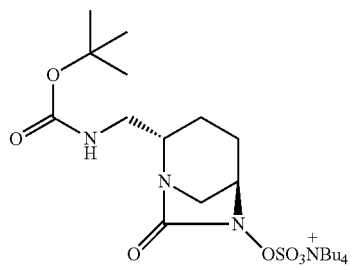
(Formula VIII)

(g) Converting a compound of Formula (VIII) to a compound of Formula (IX);

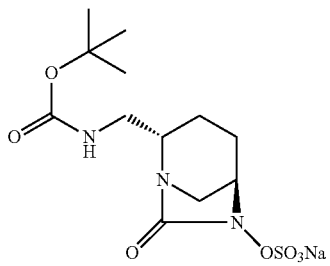
(Formula IX)

(h) Reacting a compound of Formula (IX) with trifluoroacetic acid in suitable solvent to obtain a compound of Formula (X); and

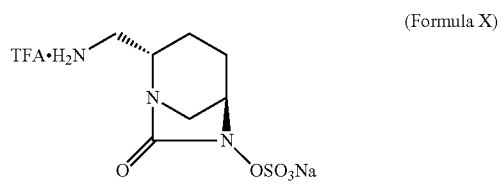
(Formula X)

(i) Converting a compound of Formula (X) to a compound of Formula (XI).

15. The compound according to claim 1, which is a compound of Formula (I) or a pharmaceutically acceptable salt thereof.

16. The compound according to claim 1, which is (2S, 5R)-6-sulfooxy-2-(aminomethyl)-7-oxo-1,6-diaza-bicyclo[3.2.1]octane or a pharmaceutically acceptable salt thereof.

17. The pharmaceutical composition according to claim 4, wherein the compound is a compound of Formula (I) or a pharmaceutically acceptable salt thereof.

18. The pharmaceutical composition according to claim 4, wherein the compound is (2S, 5R)-6-sulfooxy-2-(aminomethyl)-7-oxo-1,6-diaza-bicyclo[3.2.1]octane or a pharmaceutically acceptable salt thereof.

* * * * *